United States Patent [19]
Michaels

[11] Patent Number: 5,436,681
[45] Date of Patent: Jul. 25, 1995

[54] APPARATUS AND METHOD FOR SCREENING INDIVIDUALS FOR AMETROPIC CONDITIONS

[76] Inventor: Brian A. Michaels, 2129 Golflinks Rd., Sierra Vista, Ariz. 85635

[21] Appl. No.: 229,336
[22] Filed: Apr. 12, 1994
[51] Int. Cl.⁶ .............................................. A61B 3/02
[52] U.S. Cl. .................................. 351/240; 351/239
[58] Field of Search ............... 351/239, 240, 243, 237, 351/238, 211, 241, 242

[56] References Cited

U.S. PATENT DOCUMENTS

| | | | |
|---|---|---|---|
| 2,023,246 | 12/1935 | Sears | 88/20 |
| 2,196,904 | 4/1940 | Sherman | 351/240 |
| 2,387,442 | 10/1945 | Hamilton | 351/340 |
| 2,453,335 | 12/1948 | Morris | 88/20 |
| 3,067,647 | 12/1962 | Sato | 88/20 |
| 3,382,025 | 5/1968 | Knoll | 351/17 |
| 3,970,376 | 7/1976 | Ledi | 351/35 |
| 4,408,846 | 10/1983 | Balliet | 351/203 |
| 5,067,806 | 11/1991 | Kwasman | 351/233 |

*Primary Examiner*—William L. Sikes
*Assistant Examiner*—Hung Xuan Dang
*Attorney, Agent, or Firm*—Victor Flores

[57] ABSTRACT

A vision screening apparatus and screening method that includes a myopic screening test image and a hyperopic screening test image. In one embodiment, each screening test image includes a test letter member superimposed on a colored background member that, in combination, form the myopic screening test image portion and the hyperopic screening test image portion. In a preferred embodiment, the myopic test image is formed by a test image member, such as a letter, superimposed on a red colored background. The hyperopic screening test image is formed by a test image, such as a letter, superimposed on a green colored background. Alternatively, the test images may be colored, while the background remains a neutral color. The vision screening apparatus has applications in clinical, theater, home and office environment for methods of screening individuals to indicate whether ametropic conditions exists, such as myopia (nearsightedness), or hyperopia (farsightedness), or presbyopia (age related inability to focus at near task). The method includes determining the patient's visual acuity of the displayed myopic and hyperopic test images, and then determining which, if any, of the ametropic conditions exists. Good visual acuity of the myopic test image indicates myopia in an individual, while good visual acuity of the hyperopic test image indicates hyperopia. Good visual acuity of both test images indicates no ametropia. Use of the apparatus at less than one meter distance results in a method of screening for inability to focus at near task (presbyopia).

34 Claims, 3 Drawing Sheets

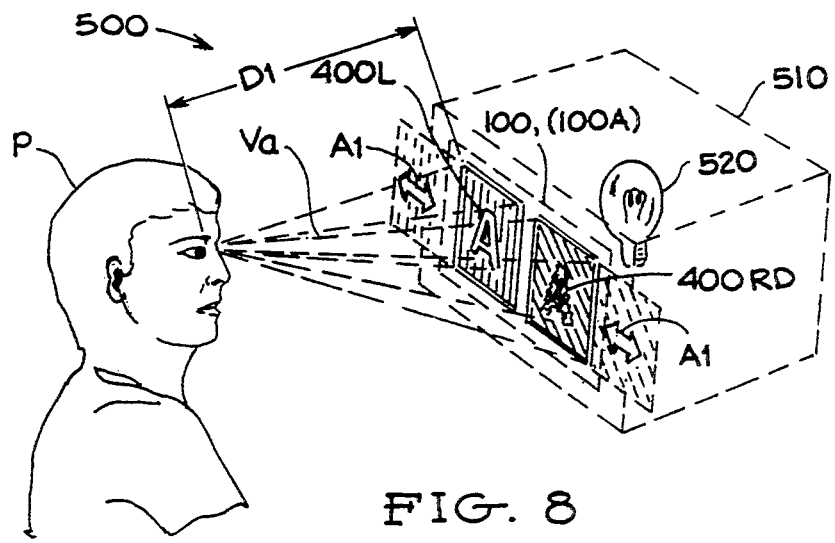
FIG. 8
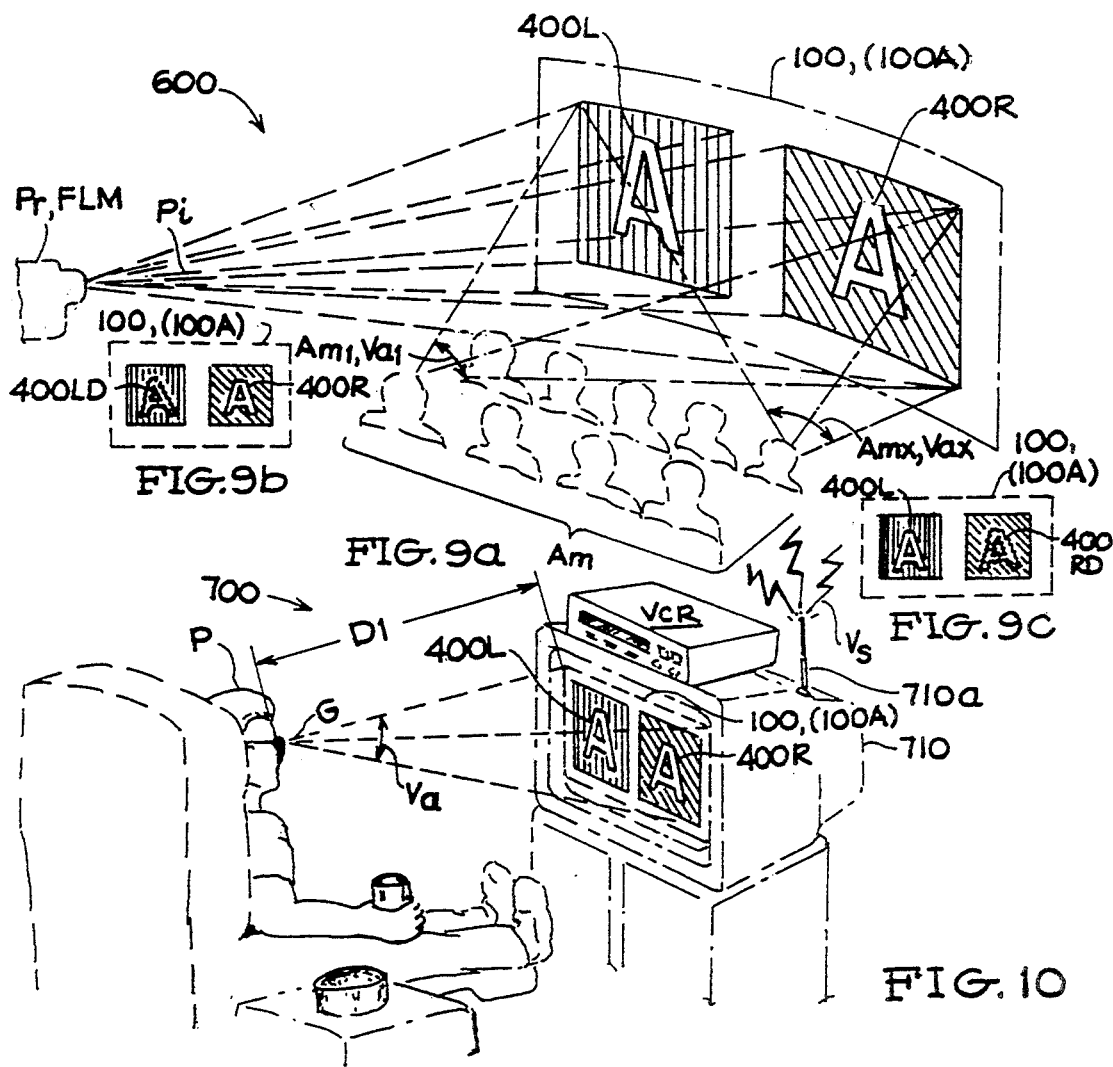
FIG. 9b
FIG. 9a
FIG. 9c
FIG. 10

APPARATUS AND METHOD FOR SCREENING INDIVIDUALS FOR AMETROPIC CONDITIONS

FIELD OF THE INVENTION

This invention relates to apparatus and methods used for ascertaining nearsighted and farsighted vision problems in individuals. More particularly, the present invention relates to apparatus and method used for examining individuals to determine whether corrective lenses are needed for nearsighted and farsighted vision problems. Even more particularly, the present invention relates to apparatus and method for screening individuals for ametropic conditions including myopia, hyperopia and presbyopia type defects.

BACKGROUND OF THE INVENTION

The traditional methods of screening for nearsighted and farsighted vision defects typically involve a series of tests on an individuals utilizing instrumentation, eye test charts, etc., to determine the individual's ability to establish visual acuity of objects at near or far distances. To applicant's knowledge specially selected colored test images have not been used to screen for nearsighted and farsighted vision defects.

Although the prior art teaches that red and green filters have been used for endpoint spherical refraction and for screening persons with color vision problems, the prior art does not teach method or apparatus for screening persons for nearsightedness or farsightedness using color as an indication of the type of visual problem of an individual.

The following group of prior art patents are related to the present invention in regards to apparatus for detecting color vision problems and in the general field of optometer technology.

| U.S. Pat. No. | Inventor | Date of Issue |
| --- | --- | --- |
| 2,023,246 | V. M. SEARS | DEC. 03, 1935 |
| 2,453,335 | R. B. MORRIS | NOV. 09, 1948 |
| 3,067,647 | KICHIRO SATO | DEC. 11, 1962 |
| 3,382,025 | H. A. KNOLL | MAY 07, 1968 |
| 3,870,376 | H. L. LEDI | JULY 20, 1976 |
| 4,408,846 | R. F. BALLIET | OCT. 11, 1983 |
| 5,067,806 | A. KWASMAN | NOV. 26, 1991 |

From this group of patents the following relate to apparatus and method for screening for color vision problems, namely U.S. Pat. Nos. 2,453,335, 3,382,025, 3,970,376 and 5,067,806. The '355 Patent to Morris and the '025 Patent to Knoll teach anomaloscope devices for testing the color vision of a subject. The structures are configured to manipulate colored light in different patterns and intensity to determine a subject's ability to distinguish between different colors produced by the structure. The '376 Patent to Ledi teaches a device for testing the color vision of a subject using a plurality of pairs of test panels of different colors. The test method associated with the '376 device facilitates distinguishing a subject's deviations from normal color perception. The '806 Patent to Kwasman teaches a device for quick screening a subject's scotopic sensitivity using colored filter and test patterns.

The prior art patents directed at optometers for use in testing for nearsightedness and farsightedness are: U.S. Pat. Nos. 2,023,246, 3,067,647, and 4,408,846. The '246 Patent to Sears teaches a bi-prism device for testing a patients eyes wherein red and green filters are used to produce different focal points. The '647 Patent to Sato teaches an optometer device, while the '846 Patent teaches a method of improving visual acuity by performing a series of predetermined steps.

In the absence of prior art teachings, the applicant has determined that an individual is nearsighted if visual acuity is better on a test pattern colored by using a red filter over the light projecting the test image, i.e. a myopic screening test image, and that an individual is farsighted if visual acuity is better on a test pattern colored by using a green filter over the light projecting the test image, i.e. a hyperopic screening test image. Further, the applicant has determined that an individual has the best corrected vision if the visual acuity is good for both red and green colored test patterns viewed by the individual. The foregoing results, while determined in a clinical environment using eye charts embodying the myopic and hyperopic test patterns, the equivalent patterns are applicable in a non-clinical environment for screening for myopia or hyperopia on an individual, or group basis.

The myopic and hyperopic test patterns of the present invention are not limited to red and green colors, but are preferred because of their relationship to the color yellow which is the color best focused on the retina. Red and green colors essentially straddle yellow in terms of wavelength of their respective emitted light ray, red having a greater wavelength than green. This relationship results in red being best focused by an individual with a myopic condition and green being best focused by an individual with a hyperopic condition.

Thus, a need is seen to exist for a vision screening apparatus configured to provide a myopic screening test image in combination with a hyperopic screening test image for use as a visual-aid in a vision screening method for detecting myopia, or hyperopia defects on an individual, or group basis.

SUMMARY OF THE INVENTION

Accordingly, the primary object of the present invention is to provide a vision screening apparatus comprising a myopic screening test image in combination with a hyperopic screening test image for use as a visual-aid in a vision screening method for detecting myopic, hyperopic and presbyopic vision defects on an individual, or group basis.

The foregoing objects are accomplished by providing a vision screening apparatus which in combination comprises a myopic screening test image and a hyperopic screening test image. The apparatus is configured in the form of a background member and at least two test image members, which are typically letters of the alphabet. The two test image members are preferably superimposed on a colored background member to form a myopic screening test image portion and a hyperopic screening test image portion. The myopic screening test image portion comprising, in a preferred embodiment, a test image, such as a letter, on a red colored background. The hyperopic screening test image portion comprising, in a preferred embodiment, a test image, such as a letter, on a green colored background. Alternatively, the test images may be colored, while the background remains a neutral color.

The vision screening apparatus is especially useful in the form of colored eye chart displayed, by example, by passing a projector's light through red and green filter onto a dual test image projected on a screen in an optometrist's office for viewing by a patient. The method includes instructing the patient to view the projected vision screening pattern, determining the patient's visual acuity of the projected myopic and hyperopic test images, and then determining whether an ametropic condition exists based on the response to the visual acuity inquiry. The visual acuity inquiry will reveal that the patient has a myopic condition, if better visual acuity of the myopic test image is the patient's response. Similarly, the visual acuity inquiry will reveal that the patient has a hyperopic condition if better visual acuity of the hyperopic test image is the patient's response. However if the patient's response is that there is good visual acuity of both myopic and hyperopic test images, then the screening indicates that the patient does not have an ametropic condition. However, further viewing of the myopic and hyperopic test images by the patient at a normal working distance of less than one meter, reveals that the patient does have an inability to focus at near task, if better visual acuity of the hyperopic test image is the patient's response to the inquiry at near distance.

Therefore, to the accomplishments of the foregoing objects, the invention consists of the foregoing features hereinafter fully described and particularly pointed out in the claims, the accompanying drawings and the following disclosure describing in detail the invention, such drawings and disclosure illustrating but one of the various ways in which the invention may be practiced.

BRIEF DESCRIPTION OF THE DRAWINGS

FIG. 8 is a perspective view of a patient viewing a lighted display apparatus displaying a representation of an eye screening chart containing myopic and hyperopic test images as viewed by an individual with a myopic condition.

FIG. 9a is a perspective view of an audience in a theater environment viewing a movie screen projection of an eye screening chart containing myopic and hyperopic test images as viewed by individual audience members without an ametropic condition.

FIG. 9b is the eye screening chart shown in FIG. 9a as viewed by an audience member with an hyperopic condition.

FIG. 9c is the eye screening chart shown in FIG. 9a as viewed by audience member with a myopic condition.

FIG. 10 shows an individual in a home environment viewing a television set displaying a video signal transmission of a myopic and hyperopic test pattern from a television station, or alternatively from a playback transmission from a video cassette recorder, illustrating a self-screening situation where the individual does not have an ametropic condition.

DESCRIPTION OF THE PREFERRED EMBODIMENT

Figure 1:
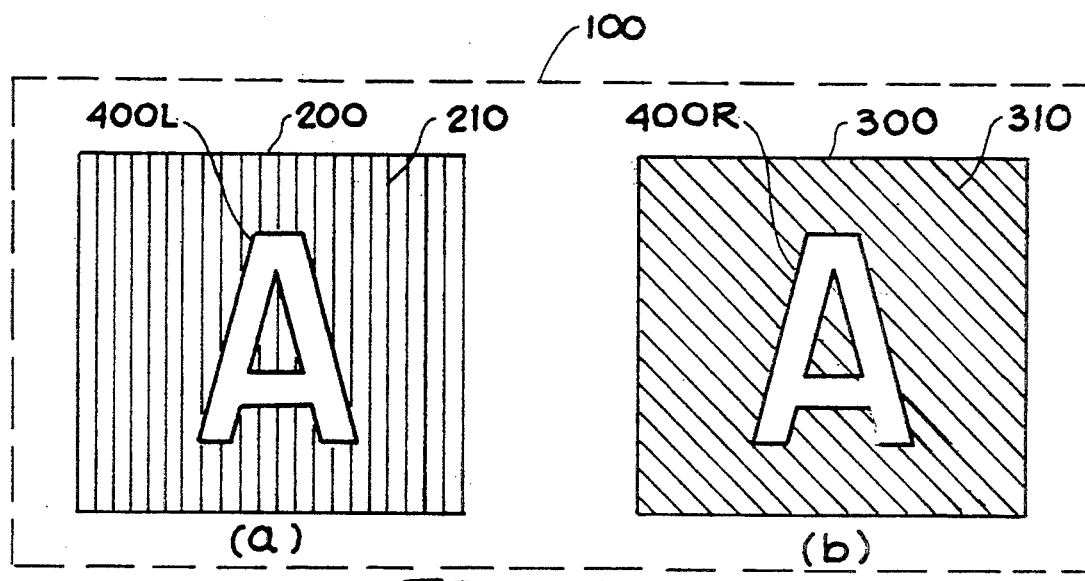
FIG. 1 is a diagram of the present invention illustrating a background colored eyechart (indicated by different striping) provided with myopic (left) and hyperopic (right) test images as viewed by an individual without an ametropic condition.
Figure 2:
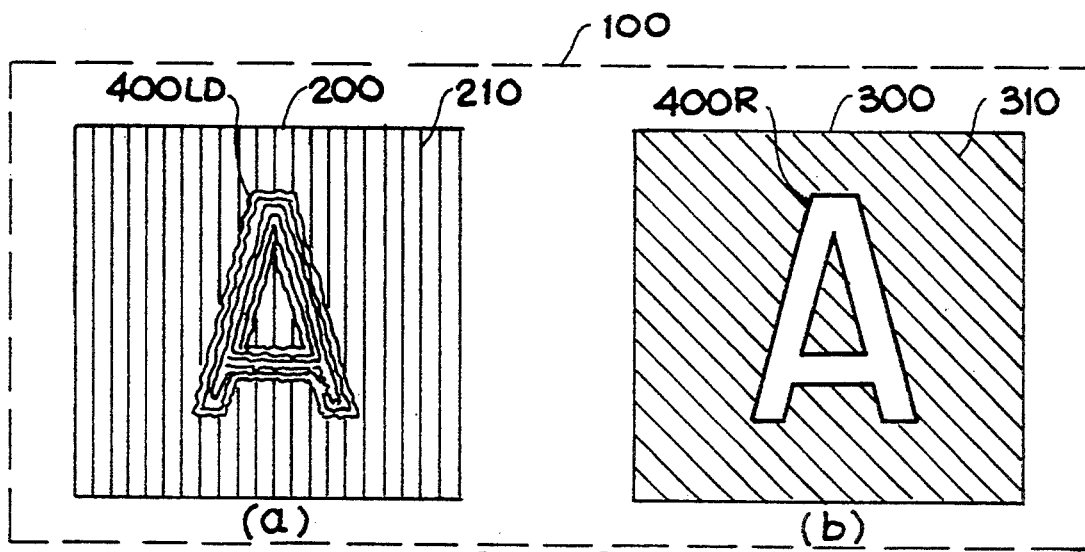
FIG. 2 is a diagram of the present invention illustrating the same eyechart depicted in FIG. 1 as viewed by an individual with a hyperopic condition.

Referring to FIG. 1 where the present invention is illustrated as an eyechart 100 having colored myopic test image 200 and colored hyperopic test image 300, color being indicated generally by vertical striping 210 and by slanted striping 310, respectively, and in the preferred embodiment vertical stripping 210 depicts red, and the slanted stripping 310 depicts green. Each colored background is provided, by example, with a respective letter A, 400L and 40OR, superimposed thereon to form myopic test image 200 and hyperopic test image 300. Thus, left portion 100(a) of eye chart 100 represents a myopic test image 200 and right portion 100(b) of eye chart 100 represents a hyperopic test image 300. FIG. 1 as illustrated represents a viewing condition as viewed by an individual without an ametropic condition.

FIG. 8 shows eyechart 100 depicted in FIG. 1 as viewed by an individual with a hyperopic condition. Here, the individual with a hyperopic condition would view chart 100 and focus clearly on the hyperopic image 300 and the test letter image 400R, but would view the myopic image 200, containing test letter image 400L, as a blurry, un-focused test image 400LD.

Figure 3:
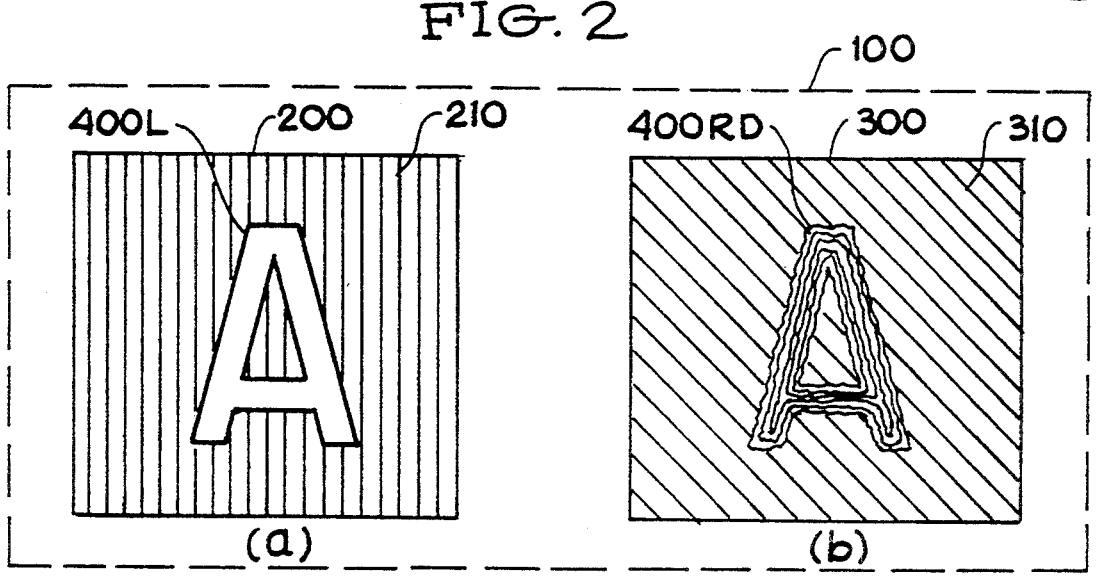
FIG. 3 is a diagram of the present invention illustrating the same eyechart depicted in FIG. 1 as viewed by an individual with a myopic condition.

Similarly, FIG. 3 shows eyechart 100 depicted in FIG. 1 as viewed by an individual with a myopic condition. Here, the individual with a myopic condition would view chart 100 and focus clearly on the myopic image 200 and the test letter image 400L, but would view the hyperopic image 300, containing test letter image 400R, as a blurry, un-focused test image 400RD.

Figure 4:
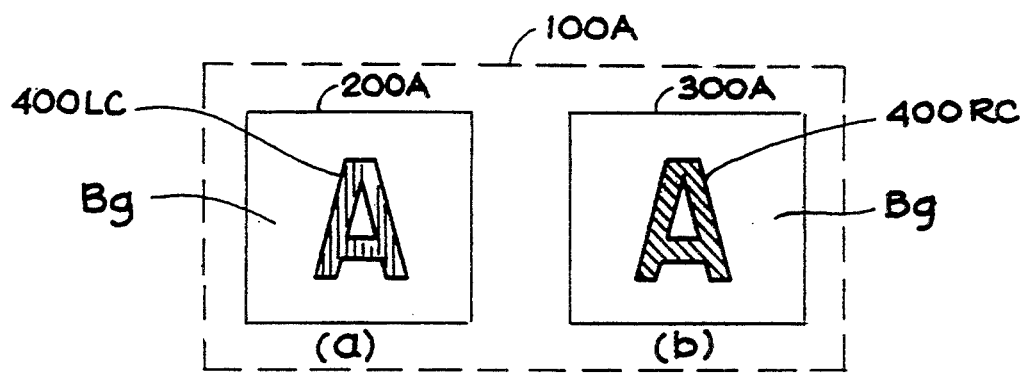
FIG. 4 is a diagram of the present invention illustrating a test image colored eyechart (indicated by different striping) provided with myopic (left) and hyperopic (right) test images as viewed by an individual without an ametropic condition.

Referring now to FIG. 4 where the present invention is illustrated as an eyechart 100A having colored myopic test image 200A and colored hyperopic test image 300A, color also being indicated generally by vertical striping 210 and by slanted striping 310, respectively. Here, as in the case for chart 100, the preferred embodiment of chart 100A comprises vertical stripping 210 depicting red, and the slanted stripping 310 depicting green. Each respective letter A, denoted as 400LC and 400RC, is superimposed on a neutral background Bg to form myopic test image 200A and hyperopic test image 300A. Thus, left portion 100A(a) of eye chart 100A represents a myopic test image 200A and right portion 100A(b) of eye chart 100A represents a hyperopic test image 300A. FIG. 4 as illustrated represents a viewing condition as viewed by an individual without an ametropic condition.

Figure 5:
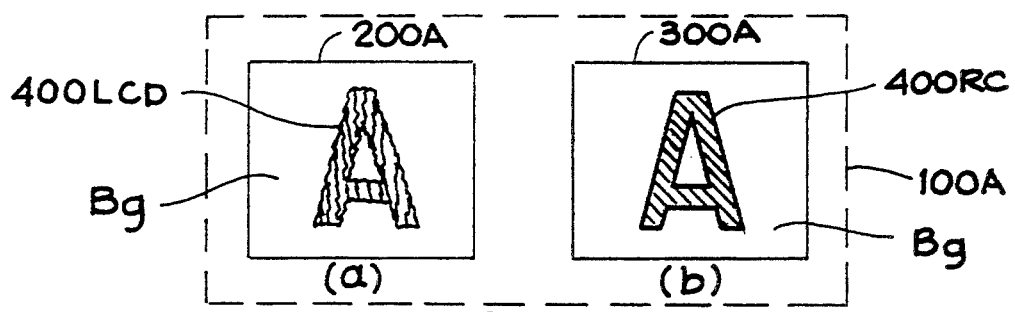
FIG. 5 is a diagram of the present invention illustrating the same eyechart depicted in FIG. 4 as viewed by an individual with a hyperopic condition.

FIG. 5 shows eyechart 100A depicted in FIG. 4 as viewed by an individual with a hyperopic condition. Here, the individual with a hyperopic condition would view chart 100A and focus clearly on the hyperopic image 300A and the test letter image 400RC, but would view the myopic image 200A, containing test letter image 400LC, as un-focused test image 400LCD.

Figure 6:
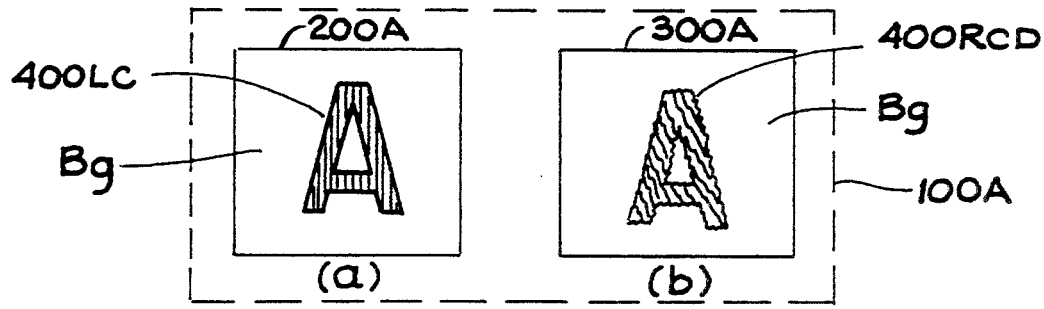
FIG. 6 is a diagram of the present invention illustrating the same eyechart depicted in FIG. 4 as viewed by an individual with a myopic condition.

Similarly, FIG. 6 shows eyechart 100A depicted in FIG. 4 as viewed by an individual with a myopic condition. Here, the individual with a myopic condition would view chart 100A and focus clearly on the myopic image 200A and the test letter image 400LC, but would view the hyperopic image 300A, containing test letter image 400RC, as un-focused test image 400RCD.

Figure 7:
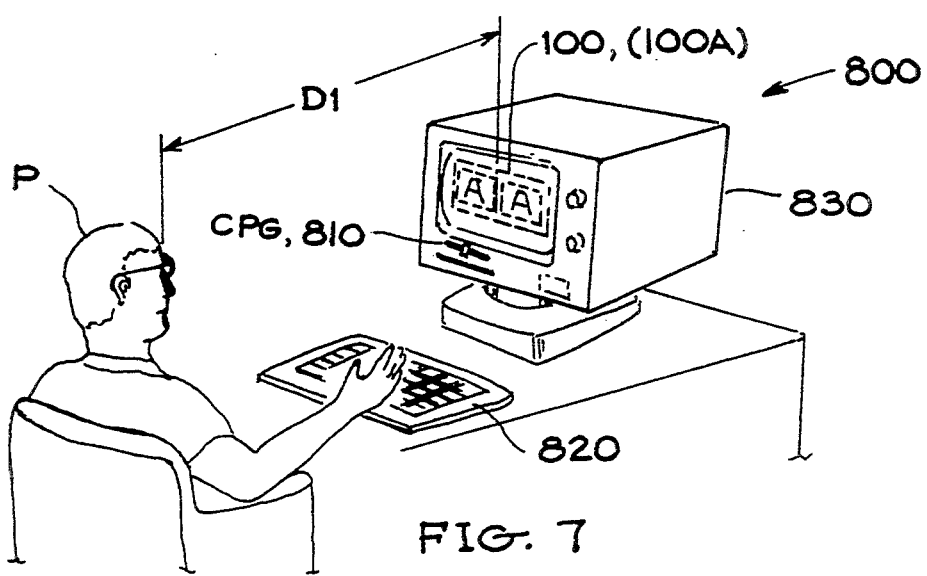
FIG. 7 is a perspective view of a computer operator viewing a computer display monitor displaying a representation of an eye screening chart containing myopic and hyperopic test images as viewed by an individual without an ametropic condition.

FIG. 7 show a personal computer system 800 in an environment for using the vision screening apparatus 100 (100A) of the present invention. Here, a computer operator P is shown operating the personal computer system 800 wherein a software operating computer program CPG containing the software coded version of vision screening apparatus 100 (100A) has been loaded into the computer's drive unit 810 for being manipulated via a keyboard 820 and displayed on a color display monitor 830. As depicted in FIG. 7, operator P has the best corrected vision and views the myopic and hyperopic test images as being equally focused at a near distance D1. The physical distance D1, by example less than 1 meter, may be used to illustrate the present invention's application for use in screening for the existence of a presbyopic vision defect. For example, if P had been previously screened and determined not to have an ametropic condition, where D1 was at least 6 meters (20 feet) and the myopic and hyperopic test images were in good focus, a re-screening at D1 being less than 1 meter may result in better visual acuity of the hyperopic test image, indicating an inability to focus at near task. The re-screening may again verify that operator P does not have a vision problem by viewing the displayed eyechart with both myopic and hyperopic images in focus.

FIG. 8 is a perspective view of a patient P viewing a lighted display apparatus 500 displaying a representation of eye screening chart 100, which could also be embodiment 100A, containing myopic and hyperopic test images 400L and 400R as viewed by P with a myopic condition. Here, at a distance D1, patient P views 400L test image in-focus while test image 400R is un-focused, depicted as 400RD. Apparatus 500 comprises an enclosure 510 and a light means 520 for illuminating through colored filter embodiments of eyecharts 100,(100A). As depicted, filter charts 100,(100A) may be slide-mounted to enclosure 510 as indicated by arrows A1.

By example only, apparatus 500 may be disposed at a distance D1 of at least 6 meters (20 feet), typical of a distance used in a clinical environment. A screening for ametropic conditions may be conducted by instructing patient P to view the displayed chart as indicated by viewing direction Va. The patient's response would reveal patient P has a myopic condition if better visual acuity of the myopic test image portion is determined. Alternatively, the patient's response would reveal that P has a hyperopic condition if better visual acuity of the hyperopic test image portion is determined. If the patient's response is that good visual acuity of both myopic and hyperopic test images is seen, then the patient does not have an ametropic condition. However, although a screening at D1 equal to at least 6 meters results in P not having an ametropic condition, a re-screening, with D1 equal to less than 1 meter, may result in P having better visual acuity of the hyperopic test image, which would indicate an inability to focus at near task. Similarly, the re-screening may again verify that there is no vision problem by operator P viewing the displayed eyechart with both myopic and hyperopic images in focus.

FIG. 9a is a larger scale vision screening application of the present invention. As illustrated, an audience Am is shown in a theater environment 600 viewing a movie screen projection of film FLM containing eye screening chart 100,(100A) comprising myopic and hyperopic test images 400L and 400R, respectively. As shown, the general audience members Am view the projected FLM image Pi from projector Pr as being in focus, indicating an ametropic condition. However, the more probable indications is that indicated in FIGS. 9(b) and 9(c). FIG. 9(b) illustrates a visual acuity image of audience member Am1 viewing the projected eyechart 100,(100A) at a viewing angle Va1 and indicating a hyperopic condition. Similarly, FIG. 9c illustrates a visual acuity image of audience member Amx viewing the projected eyechart 100,(100A) at a viewing angle Vax and indicating a myopic condition.

FIG. 10 shows the present invention in a home environment 700 where a person P is viewing a television set 710 displaying a video signal transmission Vs of screening charts 100,(100A) received at antenna 710a from a television station. Video signal Vs contains myopic and hyperopic test images 400L, 400R as part of the transmission. Alternatively, an equivalent video signal may be generated as a playback transmission from a video cassette recorder VCR. As shown in FIG. 10, the viewer P viewing the television monitor at a distance D1 and at a viewing angle Va. Here, P is shown wearing glasses G and is depicted as individual that does not have an ametropic condition and being in a best corrected vision state.

In a commercial situation outside of a clinical environment, the myopic and hyperopic test pattern may be accompanied by advertising messages from local vision care establishments. Further, the myopic and hyperopic test patterns may be provided on a handy flip-chart, or a hand-held chart.

Therefore, while the present invention has been shown and described herein in what is believed to be the most practical and preferred embodiments, it is recognized that departures can be made therefore within the scope of the invention, which is therefore not to be limited to the details disclosed herein but is to be accorded the full scope of the claims so as to embrace any and all equivalent apparatus.

I claim:

1. A method of screening for ametropic conditions, said method comprising the steps of:
   (a) providing a vision screening apparatus comprising, in combination, a myopic screening test image, and a hyperopic screening test image;
   (b) displaying said vision screening apparatus for viewing by at least one person:
   (c) instructing said at least one person to view said displayed vision screening apparatus;
   (d) determining said at least one person's visual acuity of said displayed myopic and hyperopic test images; and
   (e) determining whether an ametropic condition exists based on visual acuity test results obtained in said step (d);
   said step (a) comprises
      providing said myopic screening test image as a red colored background section and a first test image member superimposed on said red colored background section, and providing said hyperopic screening test image as a green colored background section and a second test image member superimposed on said green colored background section;

said step (e) comprises determining that said at least one person has a myopic condition if better visual acuity of said myopic test image is determined in said step (d);

said step (e) comprises determining that said at least one person has a hyperopic condition if better visual acuity of said hyperopic test image is determined in said step (d); and said step (e) comprises determining that said at least one person does not have an ametropic condition if good visual acuity of both said myopic and hyperopic test images is determined in said step (d).

2. A method of screening for ametropic conditions as described in claim 1, wherein:

after determining that said at least one person does not have an ametropic condition, said step (b) is repeated by further displaying said vision screening apparatus at a near distance from said at least one person and instructing said at least one person to view said near distance displayed vision screening apparatus, said near distance being a normal working distance of less than one meter;

said step (d) is repeated for determining said at least one person's visual acuity of said near distance displayed myopic and hyperopic test images; and said step (e) comprises determining that said at least one person that does not have an ametropic condition does have an inability to focus at near task if better visual acuity of said hyperopic test image is determined in said repeated step (d).

3. A computerized method of screening for ametropic conditions, said method comprising the steps of:

(a) providing a computer system for performing eye examinations;

(b) providing a computer program for generating a vision screening display pattern on a display monitor member of said computer system, said display pattern comprising a myopic screening test image and a hyperopic screening test image;

(c) loading said computer program into said computer system for utilization;

(d) running said computer program and displaying said vision screening display pattern for viewing by at least one person;

(e) instructing said at least one person to view said displayed vision screening display pattern;

(f) determining said at least one person's visual acuity of said displayed myopic and hyperopic test images; and (g) determining whether an ametropic condition exists based on visual acuity results obtained in said step (f).

4. A method of screening for ametropic conditions as described in claim 3, wherein:

said step (b) comprises generating said myopic screening test image on said display monitor member as a red colored background section and a first test image member superimposed on said red colored background section, and generating said hyperopic screening test image on said display monitor member as a green colored background section and a second test image member superimposed on said green colored background section;

said step (g) comprises determining that said at least one person has a myopic condition if better visual acuity of said myopic test image is determined in said step (f);

said step (g) comprises determining that said at least one person has a hyperopic condition if better visual acuity of said hyperopic test image is determined in said step (f); and said step (g) comprises determining that said at least one person does not have an ametropic condition if good visual acuity of both said myopic and hyperopic test images is determined in said step (f).

5. A vision screening apparatus for determining ametropic conditions, said apparatus comprising:

a background member, said background being equally divided into a left background section and a right background section, said left background section being colored a first color and said right background section being colored a second color;

a first test image member superimposed on said left background section; and a second test image member superimposed on said right background section, said first test image member, in combination with said left background section, forming a myopic screening test image, and said second test image member, in combination with said right background section, forming a hyperopic screening test image, said first color being characterized such that better visual acuity of said myopic screening test image, than of said hyperopic screening test image, results during a viewing session, and said second color being characterized such that better visual acuity of said hyperopic screening test image, than of said myopic screening test image, results during a viewing session.

6. A vision screening apparatus as described in claim 5, wherein:

said first and second test image members being identical test pattern images, and said first color being red, and said second color being green.

7. A test image apparatus for use in vision screening, said apparatus comprising:

a myopic screening test image; and a hyperopic screening test image.

said myopic screening test image comprises a first colored background section and a first test image member superimposed on said first colored background section; and said hyperopic screening test image comprises a second colored background section and a second test image member superimposed on said second colored background section, said first colored background section being characterized such that better visual acuity of said myopic screening test image, than of said hyperopic screening test image, results during a viewing session, and said second colored background section being characterized such that better visual acuity of said hyperopic screening test image, than of said myopic screening test image, results during a viewing session.

8. A test image apparatus as described in claim 7, wherein:
said first and second test image members being identical test pattern images, and
said first colored background section being red, and said second colored background section being green.

9. A test image apparatus as described in claim 7, wherein:
said apparatus comprises an eye chart embodiment of said myopic screening test image and said hyperopic screening test image.

10. A test image apparatus as described in claim 7, wherein:
said apparatus comprises a computer program containing a software coded version of said myopic screening test image and said hyperopic screening test image.

11. A test image apparatus as described in claim 7, wherein:
said apparatus comprises colored filter embodiments of said myopic screening test image and said hyperopic screening test image.

12. A test image apparatus as described in claim 7, wherein:
said apparatus comprises a movie film embodiment of said myopic screening test image and said hyperopic screening test image.

13. A test image apparatus as described in claim 7, wherein:
said apparatus comprises a television video signal embodiment of said myopic screening test image and said hyperopic screening test image.

14. A test image apparatus as described in claim 13, wherein:
said television video signal embodiment comprises a television station broadcast signal containing said myopic screening test image and said hyperopic screening test image.

15. A test image apparatus as described in claim 13, wherein:
said television video signal embodiment comprises a video cassette containing said myopic screening test image and said hyperopic screening test image.

16. A test image apparatus for use in vision screening, said apparatus comprising:
a myopic screening test image; and
a hyperopic screening test image,
said myopic screening test image comprises a first colored test image member superimposed on a background section; and
said hyperopic screening test image comprises a second colored test image member superimposed on said background section,
said first colored test image member being characterized such that better visual acuity of said myopic screening test image, than of said hyperopic screening test image, results during a viewing session, and
said second colored test image member being characterized such that better visual acuity of said hyperopic screening test image, than of said myopic screening test image, results during a viewing session.

17. A test image apparatus as described in claim 16, wherein:
said first and second colored test image members being identical test pattern images in all respects except as to color, and
said first colored test image member being colored red and, and said second colored test image members being green.

18. A test image apparatus as described in claim 16, wherein:
said apparatus comprises an eye chart embodiment of said myopic screening test image and said hyperopic screening test image.

19. A test image apparatus as described in claim 16, wherein:
said apparatus comprises a computer program containing a software coded version of said myopic screening test image and said hyperopic screening test image.

20. A test image apparatus as described in claim 16, wherein:
said apparatus comprises colored filter embodiments of said myopic screening test image and said hyperopic screening test image.

21. A test image apparatus as described in claim 16, wherein:
said apparatus comprises a movie film embodiment of said myopic screening test image and said hyperopic screening test image.

22. A test image apparatus as described in claim 16, wherein:
said apparatus comprises a television video signal embodiment of said myopic screening test image and said hyperopic screening test image.

23. A test image apparatus as described in claim 22, wherein:
said television video signal embodiment comprises a television station broadcast signal containing said myopic screening test image and said hyperopic screening test image.

24. A test image apparatus as described in claim 22, wherein:
said television video signal embodiment comprises a video cassette containing said myopic screening test image and said hyperopic screening test image.

25. A movie projection method of screening for ametropic conditions, said method comprising the steps of:
(a) providing a movie projector system for projecting film;
(b) providing a film containing frame images of a vision screening display pattern, said display pattern comprising a myopic screening test image and a hyperopic screening test image;
(c) projecting and displaying said vision screening display pattern onto a projection screen for viewing by at least one person;
(d) instructing said at least one person to view said displayed vision screening display pattern;
(e) determining said at least one person's visual acuity of said displayed myopic and hyperopic test images; and
(f) determining whether an ametropic condition exists based on visual acuity results obtained in said step (e);
said step (b) comprises providing said myopic screening test image on said film as a red colored background section and a first test image member superimposed on said red colored background section, and providing said hyperopic screening test image on said film as a green colored background section and a second test image member superimposed on said green colored background section;

said step (f) comprises determining that said at least one person has a myopic condition if better visual acuity of said myopic test image is determined in said step (e);

said step (f) comprises determining that said at least one person has a hyperopic condition if better visual acuity of said hyperopic test image is determined in said step (e); and said step (f) comprises determining that said at least one person does not have an ametropic condition if good visual acuity of both said myopic and hyperopic test images is determined in said step (e).

26. A movie projection method of screening for ametropic conditions, said method comprising the steps of:
(a) providing a movie projector system for projecting a film:
(b) providing a film containing frame images of a vision screening display pattern, said display pattern comprising a myopic screening test image and a hyperopic screening test image:
(c) projecting and displaying said vision screening display pattern onto a projection screen for viewing by at least one person;
(d) instructing said at least one person to view said displayed vision screening display pattern;
(e) determining said at least one person's visual acuity of said displayed myopic and hyperopic test images; and
(f) determining whether an ametropic condition exists based on visual acuity results obtained in said step (e);
said step (b) comprises providing said myopic screening test image on said film as a red colored test image member superimposed on a non-red colored background section, and providing said hyperopic screening test image on said film as a green colored test image member superimposed on a non-green colored background section;
said step (f) comprises determining that said at least one person has a myopic condition if better visual acuity of said myopic test image is determined in said step (e);
said step (f) comprises determining that said at least one person has a hyperopic condition if better visual acuity of said hyperopic test image is determined in said step (e); and
said step (f) comprises determining that said at least one person does not have an ametropic condition if good visual acuity of both said myopic and hyperopic test images is determined in said step (e).

27. A clinical method of screening for ametropic conditions, said method comprising the steps of:
(a) providing clinical instruments for examining a patient's eyes;
(b) providing an ametropic vision screening device comprising a myopic screening test image, and a hyperopic screening test image;
(c) functionally incorporating said ametropic vision screening device with said clinical instruments;
(d) manipulating said clinical instruments and displaying said ametropic vision screening device for viewing by a patient;
(e) instructing said patient to view said displayed ametropic vision screening device;
(f) determining said patient's visual acuity of said displayed myopic and hyperopic test images; and
(g) determining whether an ametropic condition exists based on visual acuity test results obtained in said step (d), wherein:
said step (b) comprises providing said myopic screening test image as a red colored background section and a first test image member superimposed on said red colored background section, and providing said hyperopic screening test image as a green colored background section and a second test image member superimposed on said green colored background section;
said step (g) comprises determining that said patient has a myopic condition if better visual acuity of said myopic test image is determined in said step (f);
said step (g) comprises determining that said patient has a hyperopic condition if better visual acuity of said hyperopic test image is determined in said step (f); and
said step (g) comprises determining that said patient does not have an ametropic condition if good visual acuity of both said myopic and hyperopic test images is determined in said step (f).

28. A clinical method of screening for ametropic conditions as described in claim 27, wherein:
after determining that said patient does not have an ametropic condition, said step (d) is repeated by further displaying said ametropic vision screening device at a near distance from said patient and instructing said patient to view said near distance displayed vision screening device, said near distance being a normal working distance of less than one meter;
said step (f) is repeated for determining said patient's visual acuity of said near distance displayed myopic and hyperopic test images; and
said step (g) comprises determining that said patient that does not have an ametropic condition does have an inability to focus at near task if better visual acuity of said hyperopic test image is determined in said repeated step (f).

29. A clinical method of screening for ametropic conditions, said method comprising the steps of:
(a) providing clinical instruments for examining a patient's eyes;
(b) providing an ametropic vision screening device comprising a myopic screening test image, and a hyperopic screening test image;
(c) functionally incorporating said ametropic vision screening device with said clinical instruments;
(d) manipulating said clinical instruments and displaying said ametropic vision screening device for viewing by a patient;
(e) instructing said patient to view said displayed ametropic vision screening device;
(f) determining said patients's visual acuity of said displayed myopic and hyperopic test images; and
(g) determining whether an ametropic condition exists based on visual acuity test results obtained in said step (d), wherein:
said step (b) comprises providing said myopic screening test image as a red colored test image member superimposed on a non-red colored background section, and providing said hyperopic screening test image as a green colored test image member superimposed on a non-green colored background section;

said step (g) comprises determining that said patient has a myopic condition if better visual acuity of said myopic test image is determined in said step (f);

said step (g) comprises determining that said patient has a hyperopic condition if better visual acuity of said hyperopic test image is determined in said step (f); and said step (g) comprises determining that said patient does not have an ametropic condition if good visual acuity of both said myopic and hyperopic test images is determined in said step (f).

30. A clinical method of screening for ametropic conditions, said method comprising the steps of:

(a) providing clinical instruments for examining a patient's eyes;

(b) providing an ametropic vision screening device comprising a myopic screening test image, and a hyperopic screening test image;

(c) functionally incorporating said ametropic vision screening device with said clinical instruments;

(d) manipulating said clinical instruments and displaying said ametropic vision screening device for viewing by a patient;

(e) instructing said patient to view said displayed ametropic vision screening device;

(f) determining said patient's visual acuity of said displayed myopic and hyperopic test images; and (g) determining whether an ametropic condition exists based on visual acuity test results obtained in said step (d), wherein:

said step (g) comprises determining that said patient does not have an ametropic condition if good visual acuity of both said myopic and hyperopic test images is determined in said step (f); and said method further comprises repeating said step (d) by further displaying said ametropic vision screening device at a near distance from said patient and instructing said patient to view said near distance displayed vision screening device, said near distance being a normal working distance of less than one meter;

said step (f) is repeated for determining said patient's visual acuity of said near distance displayed myopic and hyperopic test images; and said step (g) comprises determining that said patient has an inability to focus at near task if better visual acuity of said hyperopic test image is determined in said repeated step (f).

31. A televised method of screening for ametropic conditions, said method comprising the steps of:

(a) providing a vision screening display pattern, said display pattern comprising a myopic screening test image and a hyperopic screening test image;

(b) transmitting a colored video signal encoded version of said vision screening display pattern;

(c) receiving and displaying said transmitted video signal of said vision screening display pattern on a television receiver; for viewing by at least one person;

(d) instructing said at least one person to view said displayed vision screening display pattern;

(f) determining said at least one person's visual acuity of said displayed myopic and hyperopic test images; and (g) determining whether an ametropic condition exists based on visual acuity results obtained in said step (f).

32. A televised method of screening for ametropic conditions, as described in claim 31, wherein:

said step (a) comprises providing salad myopic screening test image as a red colored background section and a first test image member superimposed on said red colored background section, and providing said hyperopic screening test image as a green colored background section and a second test image member superimposed on said green colored background section;

said step (g) comprises determining that said at least one person has a myopic condition if better visual acuity of said myopic test image is determined in said step (f);

said step (g) comprises determining that said at least one person has a hyperopic condition if better visual acuity of said hyperopic test image is determined in said step (f); and said step (g) comprises determining that said at least one person does not have an ametropic condition if good visual acuity of both said myopic and hyperopic test images is determined in said step (f).

33. A televised method of screening for ametropic conditions, as described in claim 31, wherein:

said transmitted video signal comprises an encoded colored video signal transmitted from a video cassette recorder.

34. A televised method of screening for ametropic conditions, as described in claim 31, wherein:

said transmitted video signal comprises an encoded colored video signal transmitted from a television broadcast station.

* * * * *